United States Patent
Zhao et al.

(12)

(10) Patent No.: US 6,667,293 B1
(45) Date of Patent: *Dec. 23, 2003

(54) USE OF CYCLODEXTRINS TO MODULATE GENE EXPRESSION WITH REDUCED IMMUNOSTIMULATORY RESPONSE

(75) Inventors: Qiuyan Zhao, Worcester, MA (US); Jamal Temsamani, Worcester, MA (US); Sudhir Agrawal, Shrewsbury, MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/527,126

(22) Filed: Sep. 12, 1995

(51) Int. Cl.[7] ............................................. A01N 43/04
(52) U.S. Cl. ....................................................... 514/44
(58) Field of Search ........................ 514/44; 436/500; 424/93.1; 536/23.1, 24.5; 435/6, 7.21

(56) References Cited

U.S. PATENT DOCUMENTS

| | | |
|---|---|---|
| 5,068,227 A | * 11/1991 | Weinshenker |
| 5,149,798 A | 9/1992 | Agrawal et al. |
| 5,245,022 A | 9/1993 | Weis et al. |
| 5,248,670 A | 9/1993 | Draper et al. |
| 5,273,876 A | 12/1993 | Hock et al. |

FOREIGN PATENT DOCUMENTS

WO    WO 95/32739    12/1995

OTHER PUBLICATIONS

Arima et al., Enhanced rectal absorption and reduced local irritation of the antiflammatory drug ethyl 4–biphenylylacetate in rats by complexation wit water soluble B–cyclodextrin derivatives and formulation as oleaginous suppository, J. Pharm. Sci., vol, Nov. 1992.*
Shi et al., Transcatheter delivery of c–myc antisense oligomers reduces neointimal formation in a porcine model of coronary artery balloon injury, Circulation, vol. 90 (2), pp. 944–951, Aug. 1994.*
Uekama et al., Protective effects of cyclodextrin sulphates against gentamicin–induced nephrotoxity in the rat, J. Pharm. Pharmacol., vol. 45, pp. 745–747, 1993.*
Zhao et al., Formulation of oligonucleotides with cyclodextrins to enhance cellular uptake, Clin. Chem., vol. 40(12), p. 2339, Dec. 1994.*
Zhao et al. (1995) *Antisense Research and Development* 5:185–192.
Habus et al. (1995) *Bioconjugate Chemistry* 6 :327–331.
Tang et al. (1993) *Nucleic Acids Research* 21:2729–2735.
Krieg et al. (1995) *Nature* 374:546–549.
McIntrye et al. (1993) *Antisense Research and Development* 3:309–322.

* cited by examiner

*Primary Examiner*—Andrew Wang
*Assistant Examiner*—James Douglas Schultz
(74) *Attorney, Agent, or Firm*—Hale and Dorr LLP

(57) ABSTRACT

The present invention provides a method of reducing the immunostimulatory effects of certain phosphorothioate oligonucleotides used to treat pathogen-mediated disease states and other medical conditions. Immunostimulatory effects of phosphorothioate oligonucleotides are reduced in accordance with the method of the invention by administering the phosphorothioate oligonucleotide in a therapeutic formulation which includes at least one cyclodextrin to a mammal afflicted with the disease or condition being treated. The immune response of the mammal is also monitored in the method of the invention.

9 Claims, 7 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "phosphorothioate linked
         deoxyribonucleic acid"

(iv) ANTI-SENSE: YES (vi) ORIGINAL SOURCE:
      (A) ORGANISM: Human immunodeficiency virus type 1 gag gene (xi) SEQUENCE DESCRIPTION: SEQ ID NO:1:

CTCTCGCACC CATCTCTCTC CTTCT      25

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "phosphorothioate linked
         deoxyribonucleic acid"

(iv) ANTI-SENSE: YES (vi) ORIGINAL SOURCE:
      (A) ORGANISM: Human immunodeficiency virus type 1 rev gene (xi) SEQUENCE DESCRIPTION: SEQ ID NO:2:

TCGTCGCTGT CTCCGCTTCT TCTTGCC      27

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "phosphorothioate linked
         deoxyribonucleic acid"

(iv) ANTI-SENSE: YES

-continued

```
    (vi) ORIGINAL SOURCE:
         (A) ORGANISM: human p53

(xi) SEQUENCE DESCRIPTION: SEQ ID NO:3:

CCCTGCTCCC CCCTGGCTCC                                              20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "phosphorothioate linked
             deoxyribonucleic acid"

(iv) ANTI-SENSE: YES (vi) ORIGINAL SOURCE:
         (A) ORGANISM: env gene of murine MCF (xi) SEQUENCE DESCRIPTION: SEQ ID NO:4:

GAGAACGCTC GACCTTCGAT                                              20
```

USE OF CYCLODEXTRINS TO MODULATE GENE EXPRESSION WITH REDUCED IMMUNOSTIMULATORY RESPONSE

The present invention relates to the field of antisense pharmaceuticals, and more specifically to methods for reducing the immunostimulatory response which may be induced in treated individuals by such antisense pharmaceuticals.

BACKGROUND OF THE INVENTION

Antisense oligonucleotide technology presents an exciting new therapy for many diseases, including pathogenic infections, cancer, and inherited conditions. The field has progressed enormously over the past decade, and currently numerous clinical trials are in progress or are proposed. Antisense oligonucleotides act by binding to a target nucleic acid by Watson-Crick or Hoogsteen base-pairing. Antisense oligonucleotides may be designed to target and to inhibit any single gene within an organism's genome. For example, the oligonucleotides of SEQ ID NO:1 and SEQ ID NO:2 are phosphorothioate oligonucleotides complementary to the gag and rev regions of HIV-1 which inhibit HIV-1 replication, and the phosphorothioate oligonucleotide of SEQ ID NO:3 binds to the human p53 oncogene. The antisense approach is currently the only known strategy that has broad potential for precise and effective modulation of the expression of specific genes in a disease situation.

However, some antisense oligonucleotides containing phosphorothioate linkages exhibit an immunostimulatory response, causing B cell proliferation and/or an antibody response both in vitro and in vivo. This immunostimulatory response is not characteristic of all antisense oligonucleotides containing phosphorothioate linkages. For example, it is known that the phosphorothioate oligonucleotide of SEQ ID NO:3 does not induce an immunostimulatory effect.

Phosphorothioate oligonucleotide immunostimulatory effects appear to be dependent on particular sequences within the oligonucleotide but remain independent of whether the oligonucleotide is antisense, sense, or scrambled with respect to the respective target gene. Some phosphorothioate oligonucleotides induce cell proliferation, and other phosphorothioate oligonucleotides produce no immunostimulatory effect at all. McIntyre et al. (1993) *Antisense Res. Dev.* 3:309–322 discloses that certain oligonucleotides can cause pronounced splenomegaly in athymic nude mice. Messina et al. (1993) *Cell Immunol.* 147:148–157; and Pisetsky et al. (1994) *Life Sciences* 54:101–107 disclose that DNA as well as structurally related synthetic oligonucleotides and polynucleotides stimulate lymphocytes, but the mechanism for this stimulation is still not fully understood. B cells are usually activated from the resting state by antigen binding to surface immunoglobulin. In mice, activation can also be modulated by physiological mediators, such as interleukin-2 (IL-2), interleukin-4 (IL-4), γ-interferon, and non-physiological mitogens, such as lipopolysaccharide (LPS), Concanavalin A (con A), and pokeweed mitogen (PWM).

Certain sequence motifs or structures of oligonucleotides may play important roles in causing stimulation of murine cells. Kuramoto et al. (1992) *Jpn. J. Cancer Res.* 83:1128–1131 discloses that the presence of particular palindromic sequences including 5'-CG-3' motif(s) is a critical determinant in oligonucleotides for induction of natural killer cell activation and interferon production. Krieg et al. (1995) *Nature* 374:546–549 discloses that optimal B cell activation requires a DNA motif in which an unmethylated CpG dinucleotide is flanked by two 5'-purines and two 3'-pyrimidines.

Because of the continued need for specific treatments for diseases and inherited conditions, and the high level of specificity provided through use of antisense therapeutics capable of modulating the expression levels of targeted genes, a need exists for reducing the immunostimulatory response induced by certain phosphorothioate oligonucleotides.

Some cyclodextrins, also known as cycloamyloses, and various substituted derivatives thereof, such as hydroxypropyl-, hydroxyethyl-, methyl-, or sulfate-substituted cyclodextrins, have the ability to enhance the solubility and availability of a variety of pharmacological agents. For example, 2-hydroxypropyl β-cyclodextrin (HPCD) substantially enhances solubility and uptake of some sparingly soluble drugs such as hydrophobic protein containing drugs (Brewster et al. (1991) *Pharmaceut. Res.* 8:792–795; Yaksh et al. (1991) *Life Sci.* 48:623–633) such as insulin (Merkus et al. (1991) *Pharmaceut. Res.* 8:588–592), bovine growth hormone (Simpkins et al. (1991) *J. Parenteral Sci. Technol.* 45:266–269), and methyltestosterone (Muller et al. (1991) *J. Pharmaceut. Sci.* 80:599–604). In addition, ethylated-β-cyclodextrin has been used as slow-release type carriers for hydrophilic drugs such as diltiazem (Horiuchi et al. (1990) *J. Pharmaceut. Sci.* 79:128–132). Cyclodextrins have also been found to eliminate some of the undesirable side-effects of the drugs to which they have been complexed. For example, when used as a vehicle for rectal absorption, HPCD can suppress the local irritation of certain drugs (Arima et al. (1992) *J. Pharmaceut. Sci.* 81:1119–1125).

Other cyclodextrins have unique biological features. For example, cyclodextrin sulfates have anti-inflammatory, antilipemic, and antiviral activity, and have been found to inhibit replication of HIV by either prevention of viral absorption or budding (Pitha et al. (1991) *J. Pharmaceutic. Res.* 8:1151–1154; Anand et al. (199) *Antiviral Chem. Chemother.* 1:41–46); Moriya et al. (1991) *J. Med. Chem.* 34:2301–2304; Weiner et al. (1992) *Pathobiol.* 60:206–212). In addition, cyclodextrin sulfates have protective effects on the gentamicin-induced nephrotoxicity (Uekama et al. (1993) *J. Pharm. Pharmacol.* 45:745–747) and on hemolysis of erythrocytes (Weisz et al. (1993) *Biochem. Pharmacol.* 45:1011–1016).

Since cyclodextrins are biocompatible polymers composed of naturally occurring D-glucose subunits, their therapeutic application has been regarded are relatively safe. Indeed, in vivo administration of cyclodextrin concentrations of 5 to 10% has been generally used to enhance adsorption of drugs in animal studies, and no significant cytotoxic effects have been reported. (Gerloczy et al. (1994) *J. Pharmaceut. Sci.* 83:193–196). Besides standard intravenous administration, cyclodextrins can be easily absorbed through nasal (Merkus et al. (1991) *Pharm. Res.* 8:588–592; Shao et al. (1992) *Pharm. Res.* 9:1157–1163), intestinal (Nakanishi et al. (1992) *Chem. Pharm. Bull.* 40:1252–1256), corneal (Jansen et al. (1990) *Lens Eye Tox. Res.* 7:459–468), rectal epithelium (Arima et al. (1992) *J. Pharm. Soc. Japan* 112:65–72) routes, and by transdermal injection (Yoshida et al. (1990) *Chem. Pharm. Bull.* 38:176–179).

However, cyclodextrins have not been known to alter the effects of drugs which stimulate the mammalian immune system.

SUMMARY OF THE INVENTION

The present inventors have discovered a method of reducing the immunostimulatory effects of certain phosphorothioate oligonucleotides by adding a cyclodextrin to the pharmaceutical formulation containing the phosphorothioate oligonucleotide In one embodiment, the invention provides a method of reducing an immunostimulatory response of a mammal to a phosphorothioate oligonucleotide which comprises the steps of administering a therapeutic formulation containing the phosphorothioate oligonucleotide and at least one cyclodextrin to the mammal; and monitoring the immune response of the mammal.

In another embodiment, the invention provides a method of reducing an immunostimulatory response of a mammal to a protein which comprises the steps of administering a therapeutic formulation containing the protein and at least one cyclodextrin to the mammal; and monitoring the immune response of the mammal. In one embodiment, the formulation comprises a protein-cyclodextrin complex.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

Figure 1:
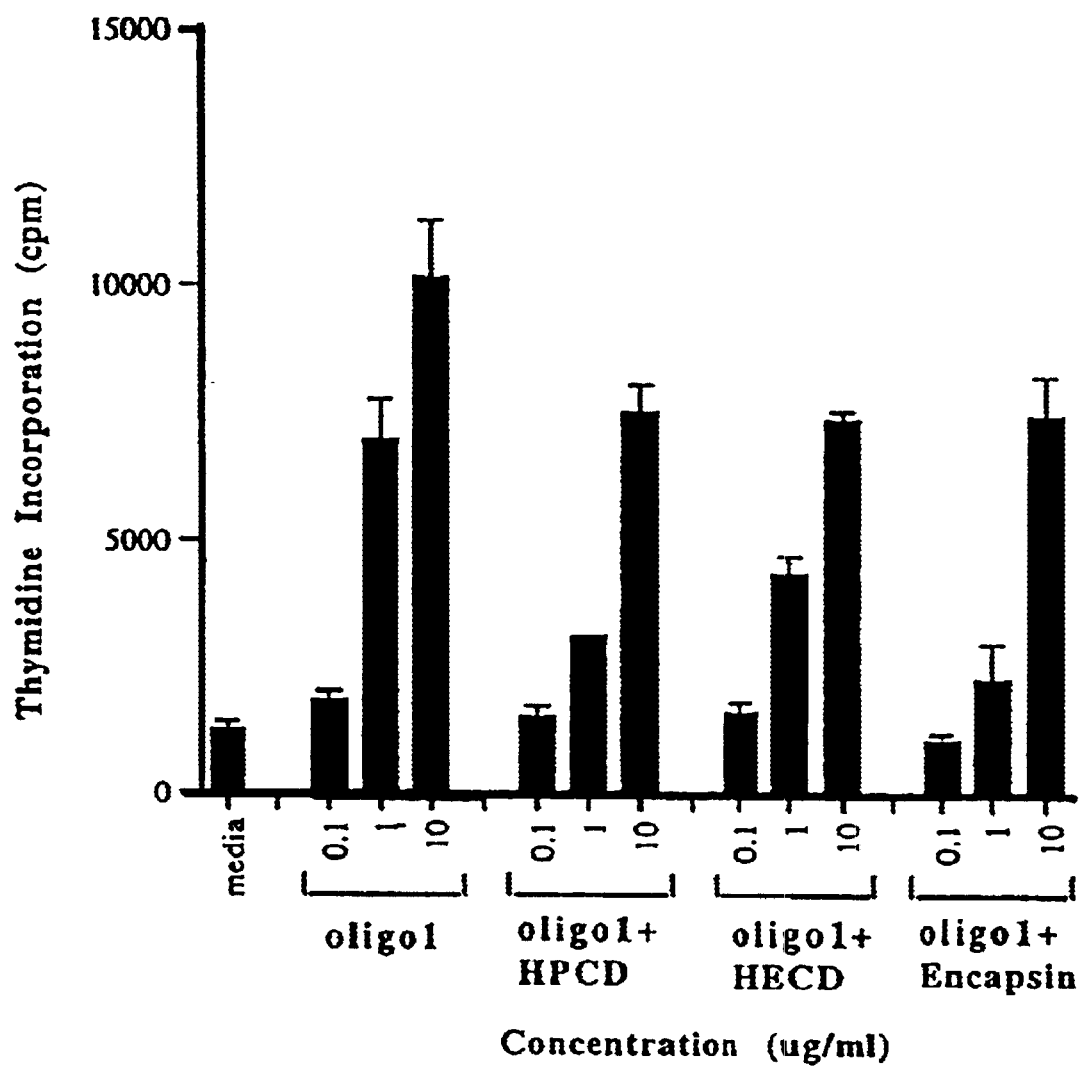
FIG. 1 shows the effect of cyclodextrins on cell proliferation induced by the phosphorothioate oligonucleotide of SEQ ID NO:2. Results are presented as means±standard deviation of a triplicate experiment.

The patent and scientific literature referred to herein establishes the knowledge that is available to those with skill in the art. The issued U.S. patent and allowed applications cited herein are hereby incorporated by reference.

In accordance with the method of the invention, at least one cyclodextrin is used to reduce an immunostimulatory response induced by a phosphorothioate oligonucleotide or a protein. In the absence of at least one cyclodextrin, the phosphorothioate oligonucleotide or protein induces an immunostimulatory response. In the first step of the method of the invention, a therapeutic formulation of a phosphorothioate oligonucleotide or protein and at least one cyclodextrin is administered to a mammal. In the second step of the method of the invention, the immune response of the mammal is monitored.

Any immunostimulatory response induced by any phosphorothioate oligonucleotide or protein may be reduced in accordance with the method of the invention. Those of skill in the art may determine whether a phosphorothioate oligonucleotide or protein induces an immunostimulatory response in a mammal using methods such as those set forth in Examples 2 through 4 below, or by using other known methods. For example, any of the methods set forth in McIntyre, et al., supra, Messina et al., supra, Pisetsky et al, supra, Kuramoto et al., supra, or Krieg et al., supra, may be used to determine whether a phosphorothioate oligonucleotide or protein induces an immunostimulatory response. In addition, immunostimulatory sequences of phosphorothioate oligonucleotides, for example, those identified in Kuramoto, et al., supra, or in Krieg, et al., supra, may be identified by inspection of the sequence of the phosphorothioate oligonucleotide.

Cyclodextrins suitable for combining with phosphorothioate oligonucleotides or protein, in a therapeutic formulation in accordance with the method of the invention include any of a group of cyclic polysaccharides consisting of six to eight naturally occurring D(+)-glucopyranose units in α-(1,4) linkage. Cyclodextrins are classified by the number of the glucose units they contain: alpha (α)-cyclodextrin has six glucose units; beta (β)-cyclodextrin has seven, and gamma (γ)-cyclodextrin has eight (Brewster et al. (1989) *J. Parenteral Sci. Technol.* 43:231–240). Any one or more of these cyclodextrin derivatives is suitable for inclusion in the therapeutic formulation used in the method of the invention to reduce an immunostimulatory response induced by a phosphorothioate oligonucleotide. Cyclodextrins can be prepared by methods known in the art (see. e.g., Moriya et al. (1993) *J. Med. Chem.* 36:1674–1677) and are commercially available.

In accordance with the method of the invention, any cyclodextrin may be used to reduce an immunostimulatory response induced by a phosphorothioate oligonucleotide, so long as the target gene expression modulating activity of the oligonucleotide is maintained. For purposes of the invention, gene modulating activity occurs by virtue of complementarity of the phosphorothioate oligonucleotide to a DNA sequence within the target gene or by virtue of complementarity of the phosphorothioate oligonucleotide to an RNA sequence transcribed from the target gene. The term "complementarity" is intended to mean that the phosphorothioate oligonucleotide and the immunostimulatory response-reducing cyclodextrin oligonucleotide bind to the target nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means, including in the case of an oligonucleotide binding to RNA, causing pseudoknot formation. Binding by Watson-Crick or Hoogsteen base pairing under physiological conditions is measured as a practical matter by observing interference with the function of the nucleic acid sequence.

The gene modulating activity of the phosphorothioate oligonucleotide is maintained in accordance with the invention when the phosphorothioate oligonucleotide in the cyclodextrin-containing therapeutic formulation is capable of changing the activity of the gene to which the phosphorothioate oligonucleotide is targeted to any degree. Preferably, the phosphorothioate oligonucleotide in the cyclodextrin-containing therapeutic formulation is capable of modulating the activity of a target gene when the target gene is expressed at a level of about 10–90% of its steady state disease expression level. More preferably, the phosphorothioate oligonucleotide in the cyclodextrin-containing therapeutic formulation is capable of modulating the activity of a target gene when the target gene is expressed at a level of less than about 50% of its steady state disease expression level. Most preferably, the phosphorothioate oligonucleotide in the cyclodextrin-containing therapeutic formulation is capable of modulating the activity of a target gene when the target gene is not detectably expressed. The steady state disease expression level of a target gene may be determined using known methods, for example, by measuring the amount of the protein encoded by the target gene in the affected mammal or in a cell or fluid derived from the affected mammal. When the target gene is present in the genome of a pathogenic organism infecting the mammal, the steady state disease expression level of a target gene may be determined by measuring the amount of the pathogenic organism shed by the infected mammal or by measuring a symptom of the infected mammal which correlates with the amount of the pathogenic organism within the mammal.

As used herein, a "phosphorothioate oligonucleotide" includes chemically synthesized polymers of about five and up to about 50, preferably from about 15 to about 30 deoxyribonucleoside and/or ribonucleoside monomers connected together or linked by at least one, and preferably more than one, 5' to 3' phosphorothioate internucleotide linkage as those terms are understood in the art. The phosphorothioate linkages may be mixed Rp and Sp enantiomers, or they may be stereoregular or substantially stereoregular in either Rp or Sp form (see Iyer et al. (1995) *Tetrahedron Asymmetry* 6:1051–1054). Phosphorothioate oligonucleotides which may be combined with at least one cyclodextrin in a therapeutic formulation are composed of deoxyribonucleotides, ribonucleotides, or a combination of both deoxyribonucleotides and ribonucleotides. Phosphorothioate oligonucleotides can be prepared by art recognized methods such as phosphoramidate or H-phosphonate chemistry which can be carried out manually or by an automated synthesizer as described by Brown in *A Brief History of Oligonucleotide Synthesis. Protocols for Oligonucleotides and Analogs, Methods in Molecular Biology* (1994) 20:1–8).

The phosphorothioate oligonucleotides may also be modified in a number of ways without compromising their ability to hybridize to the target nucleic acid. For example, the phosphorothioate oligonucleotides may contain a number of linkages which differ from the phosphorothioester internucleotide linkages between the 5' end of one nucleotide and the 3' end of another nucleotide in which the 5' nucleotide phosphate has been replaced with any number of chemical groups. Examples of such chemical groups include alkylphosphonates, phosphorodithioates, alkylphosphonothioates, alkylphosphonates, phosphoramidates, phosphate esters, carbamates, acetamidate, carboxymethyl esters, carbonates, and phosphate triesters. Phosphorothioate oligonucleotides with these linkages can be prepared according to known methods (see, e.g., Sonveaux "Protecting Groups in Oligonucleotides Synthesis" in Agrawal (1994) *Methods in Molecular Biology* 26:1–72; Uhlmann et al. (1990) *Chem. Rev.* 90:543–583).

Other modifications include those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified phosphorothioate oligonucleotides may contain at least one 2'-substituted ribonucleotide in which the 2'-OH of the ribose molecule is substituted with an —O— lower alkyl containing 1–6 carbon atoms, aryl or substituted aryl or allyl having 2–6 carbon atoms, e.g., 2'-O-allyl, 2'-O-aryl, 2'-O-alkyl (such as a 2'-O-methyl), 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups.

Yet other modified phosphorothioate oligonucleotides may be capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

Phosphorothioate oligonucleotides which are self-stabilized are also considered to be modified phosphorothioate oligonucleotides which may induce an immunostimulatory response which may be reduced by addition of cyclodextrins in accordance with the method of the invention (Tang et al. (1993) *Nucleic Acids Res.* 20:2729–2735). Such phosphorothioate oligonucleotides comprise two regions: a target hybridizing region; and a self-complementary region having an oligonucleotide sequence complementary to a nucleic acid sequence that is within the self-stabilized oligonucleotide.

The preparation of these unmodified and modified phosphorothioate oligonucleotides is well known in the art (reviewed in Agrawal et al. (1992) *Trends Biotechnol.* 10:152–158). For example, nucleotides can be covalently linked using art-recognized techniques such as phosphoramidate, H-phosphonate chemistry, or methylphosphoramidate chemistry (see, e.g., Uhlmann et al. (1990) *Chem. Rev.* 90:543–584; Agrawal et al. (1987) *Tetrahedron. Lett.* 28:(31):3539–3542); Caruthers et al. (1987) *Meth. Enzymol.* 154:287–313; U.S. Pat. No. 5,149,798). Oligomeric phosphorothioate analogs can be prepared using methods well known in the field such as methoxyphosphoramidite (see, e.g., Agrawal (1988) *Proc. Natl. Acad. Sci. (USA)* 85:7079–7073) or H-phosphonate chemistry (see, e.g., Froehler, "Oligonucleotide Synthesis: H-phosphonate Approach" in Agrawal (1994) *Meth. Mol. Biol.* 20:63–80).

The phosphorothioate oligonucleotide can be noncovalently complexed to a cyclodextrin by mixing them together in an aqueous solution such as a cellular growth medium or various buffers. Alternatively, the phosphorothioate oligonucleotide can be covalently linked to an adamantane molecule which is then noncovalently linked to the cyclodextrin. Adamantane enters into the cavity of a cyclodextrin and forms a stable, noncovalent complex with it (Brinker et al. (1993) *Angew. Chem., Int. Ed. Engl.* 32:1344–1345, Ueno et al. (1993) *J. Am. Chem. Soc.* 115:12575–12576).

Linkage of the adamantane molecule can be accomplished at the 3'-hydroxyl or 5' amino terminus of a phosphorothioate oligonucleotide having a (or both) deoxyribonucleotide terminal residue(s) termini. Alternatively, adamantane can be covalently complexed with the 2'-hydroxyl of a ribonucleotide residue. This can be accomplished with a linker phosphoramidite or H-phosphonate as the final coupling step in machine-aided assembly of an oligonucleotide, as has been used for the attachment of single reporter groups to a synthetic oligonucleotide (see, e.g., Agrawal et al. (1986) *Nucleic Acids Res.* 14:6229–6245; Misiura et al. (1990) *Nucleic Acids Res.* 18:4345–4354; Nelson et al. (1992) *Nucleic Acids Res.* 20:6253–6259).

Covalent linkage of adamantane to the phosphorothioate oligonucleotide can also be accomplished with the aid of an amino linker as described by Misiura et al. (*J. Nucleic Acids Res.* (1990) 18:4345–4353). The adamantane-linked phosphorothioate oligonucleotide is then noncovalently associated with the cyclodextrin by mixing the two in an aqueous medium or buffer (see, e.g., Simpkins et al. (1991) *J. Parental Sci. & Technol.* 45:266).

The phosphorothioate oligonucleotides are used in the method of the invention for treating pathogenic infections, for treating diseases having a genetic component such as cancer, for treating an inherited condition, and the like. Phosphorothioate oligonucleotides are used in accordance with the invention as part of a therapeutic formulation, in combination with a cyclodextrin and a physiologically and/or pharmaceutically acceptable carrier. The characteristics of the carrier will depend on the route of administration. Such a formulation may contain, in addition to the phosphorothioate oligonucleotide, at least one cyclodextrin, and carrier, diluents, fillers, salts, buffers, stabilizers, solubilizers, and other materials well known in the art. The therapeutic formulation used in the method of the invention may also contain other active factors and/or agents which enhance the activity of the phosphorothioate oligonucleotides. For example, combinations of phosphorothioate oligonucleotides, each of which is directed to a different region of a pathogen genome or to a different region of an overexpressed target gene, may be used in a therapeutic formulation containing cyclodextrin in accordance with the invention. Phosphorothioate oligonucleotides and at least one cyclodextrin may be combined with other synthetic oligonucleotides within the therapeutic formulation in accordance with the invention. The therapeutic formulation may further contain other chemotherapeutic drugs for the treatment of the disease or condition of the afflicted mammal. Such additional factors and/or agents may be included in the therapeutic formulation in accordance with the method of the invention to produce a synergistic effect with the phosphorothioate oligonucleotide, or to minimize side-effects caused by the phosphorothioate oligonucleotide. Conversely, oligonucleotides may be included in formulations of a particular factor and/or agent used to treat the disease or condition of the afflicted mammal, to minimize side effects of the factor and/or agent.

The therapeutic formulation used in the method of the invention may be in the form of a liposome in which the phosphorothioate oligonucleotides and at least one cyclodextrin are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323. The therapeutic formulation used in the method of the invention may further include other lipid carriers, such as lipofectin (Bennett et al. (1992) *Mol. Pharmacol.* 41:1023–1033)) and the like, which enhance delivery of oligonucleotides into cells, or such as slow release polymers.

As used herein, the term "therapeutically effective amount" means the total amount of each active component of the pharmaceutical formulation or method that is sufficient to show a meaningful subject or patient benefit, i.e., healing of disease conditions characterized by the disease being treated and/or an increase in rate of healing of such conditions, a reduction in the expression of proteins or cells which cause or characterize the disease or disorder being treated (e.g., in the case of a virus, a decrease in virus load over baseline under disease conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

A "therapeutically effective manner" refers to a route, duration, and frequency of administration of the pharmaceutical formulation which ultimately results in meaningful patient benefit, as described above. In some embodiments of the invention, the pharmaceutical formulation is administered via injection, sublingually, rectally, intradermally, orally, or enterally in bolus, continuous, intermittent, or continuous, followed by intermittent regimens.

The therapeutically effective amount of synthetic oligonucleotide in the pharmaceutical composition of the present invention will depend upon the nature and severity of the condition being treated, and on the nature of prior treatments which the patent has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the dosages of the pharmaceutical compositions administered in the method of the present invention should contain about 0.1 to 5.0 mg/kg body weight per day, and preferably 0.1 to 2.0 mg/kg body weight per day. When administered systemically, the therapeutic composition is preferably administered at a sufficient dosage to attain a blood level of oligonucleotide from about 0.01 $\mu$M to about 10 $\mu$M. Preferably, the concentration of oligonucleotide at the site of aberrant gene expression should be from about 0.01 $\mu$M to about 10 $\mu$M, and most preferably from about 0.05 $\mu$M to about 5 $\mu$M. However, for localized administration, much lower concentrations than this may be effective, and much higher concentrations may be tolerated. It may be desirable to administer simultaneously or sequentially a therapeutically effective amount of one or more of the therapeutic compositions of the invention when individual as a single treatment episode.

Administration of pharmaceutical compositions in accordance with invention or to practice the method of the present invention can be carried out in a variety of conventional ways, such as by oral ingestion, enteral, rectal, or transdermal administration, inhalation, sublingual administration, or cutaneous, subcutaneous, intramuscular, intraocular, intraperitoneal, or intravenous injection, or any other route of administration known in the art for administrating therapeutic agents.

When the composition is to be administered orally, sublingually, or by any non-injectable route, the therapeutic formulation will preferably include a physiologically acceptable carrier, such as an inert diluent or an assimilable edible carrier with which the composition is administered. Suitable formulations that include pharmaceutically acceptable excipients for introducing compounds to the bloodstream by other than injection routes can be found in Remington's Pharmaceutical Sciences (18th ed.) (Genarro, ed. (1990) Mack Publishing Co., Easton, Pa.). The oligonucleotide and other ingredients may be enclosed in a hard or soft shell gelatin capsule, compressed into tablets, or incorporated directly into the individual's diet. The therapeutic compositions may be incorporated with excipients and used in the form of ingestible tablets, buccal tablets, troches, capsules, elixirs, suspensions, syrups, wafers, and the like. When the therapeutic composition is administered orally, it may be mixed with other food forms and pharmaceutically acceptable flavor enhancers. When the therapeutic composition is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are also contemplated such as those described in U.S. Pat. Nos. 4,704,295, 4,556,552, 4,309,404, and 4,309,406.

When a therapeutically effective amount of composition of the invention is administered by injection, the synthetic oligonucleotide will preferably be in the form of a pyrogen-free, parenterally-acceptable, aqueous solution. The preparation of such parenterally-acceptable solutions, having due regard to ph, isotonicity, stability, and the like, is within the skill in the art. A preferred pharmaceutical composition for injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption. Sterile injectable solutions are prepared by incorporating the oligonucleotide in the required amount in the appropriate solvent, followed by filtered sterilization.

The pharmaceutical formulation can be administered in bolus, continuous, or intermittent dosages, or in a combination of continuous and intermittent dosages, as determined by the physician and the degree and/or stage of illness of the patient. The duration of therapy using the pharmaceutical composition of the present invention will vary, depending on the unique characteristics of the oligonucleotide and the particular therapeutic effect to be achieved, the limitations inherent in the art of preparing such a therapeutic formulation for the treatment of humans, the severity of the disease being treated and the condition and potential idiosyncratic response of each individual patient. Ultimately the attending physician will decide on the appropriate duration of intravenous therapy using the pharmaceutical composition of the present invention.

In practicing the method of the present invention, a therapeutically effective amount of one or more phosphorothioate oligonucleotides and at least one cyclodextrin is administered to a subject afflicted with the disease or condition being treated. The therapeutic formulation of the invention may be administered in accordance with the method of the invention either alone or in combination with other known therapies for the disease or condition being treated. When co-administered with one or more other therapies, the therapeutic formulation of the invention may be administered either simultaneously with the other treatment(s), or sequentially. If administered sequentially, the attending physician will decide on the appropriate sequence of administering the therapeutic formulation of the invention in combination with the other therapy.

It may be desirable at times to use a mixture of different phosphorothioate oligonucleotides targeting different conserved sites within a given pathogen genome or target gene. Such a mixture of phosphorothioate oligonucleotides may be in the form of a therapeutic composition comprising at least one, and preferably two or more phosphorothioate oligonucleotides in a single therapeutic formulation (i.e., a composition comprising a physical mixture of at least two phosphorothioate oligonucleotides), along with at least one cyclodextrin. These phosphorothioate oligonucleotides may have the same or different sequences. At least one, preferably two or more phosphorothioate oligonucleotides may be administered simultaneously or sequentially as a single treatment episode in the form of separate therapeutic formulations.

The following examples illustrate the preferred modes of making and practicing the present invention, but are not meant to limit the scope of the invention since alternative methods may be used to obtain similar results.

EXAMPLE 1

Preparation of Oligonucleotide—Cyclodextrin Complexes

The phosphorothioate oligodeoxynucleotides of SEQ ID NO:2 and SEQ ID NO:4 were synthesized on an automated synthesizer (Millipore, 8700, Bedford, Mass.) using phosphoramidite chemistry (Beaucage (1993) In S. Agrawal (eds), *Methods in Molecular Biology: Protocols for oligonucleotides and analogs,* Humana Press, New Jersey, pp. 33–62). The oligonucleotides were deprotected by treatment with concentrated ammonium hydroxide at 55° C. for 12 hours and were purified by reverse phase HPLC as described in Padmapriya et al. (1994) *Antisense Research & Dev.* 4:185–199.

Oligonucleotides (final concentration 4 mg/ml) were mixed with 5% of 2-hydroxypropyl-β-cyclodextrin or of 2-hydroxyethyl-β-cyclodextrin in sterile phosphate buffered saline, sonicated at 4° C. for one hour and incubated at 4° C. overnight.

EXAMPLE 2

Splenic Cell Proliferation Assays

Mouse spleen was taken from male CD1 mouse (4–5 weeks, Charles River, Wilmington, Mass.). Single cell suspensions were prepared by gently mincing with frosted ends of glass slides, washed twice, and then resuspended in RPMI complete medium [RPMI 1640 medium supplemented with 10%-heat inactivated (56° C. for 30 minutes) fetal bovine serum, 2 mM glutamine, 100 μg/ml streptomycin, 100 U/ml penicillin, and 50 μM 2-mercaptoethanol]. The cells were then plated in 96-well dishes at a density of $10^6$ cells/ml, in a final volume of 100 μl. Oligonucleotides were added to the cell culture in 10 μl of TE buffer (10 mM Tris-HCL pH 7.5, 1 mM EDTA). Cyclodextrin analogs: 2-hydroxypropyl-βcyclodextrin (HPCD, degree of substitution 5–8), hydroxyethyl-β cyclodextrin (HECD, degree of substitution 15), and Encapsin (which is a mixture of hydroxypropyl β-cyclodextrin but has a different degree of substitution, 17.8), were purchased pyrogen free (Amaizo, Hammond, Ind.) and were added to the cells at concentration of 0.5% in RPMI medium except where indicated. Cells were then set to culture in a 37° C., 5% $CO_2$-95% $O_2$, humidified air incubator for further studies. The experiments were done in triplicate.

A. Thymidine Incorporation Studies

After 44 hours, cells were pulsed-labeled with 1 μCi [$^3$H]-thymidine/well (in 20 μl of RPMI medium) for 4 hours. Cells were then harvested by an automatic cell harvester (Skatron, Sterling, Va.) and the filters were counted using a scintillation counter. The phosphorothioate oligonucleotide of SEQ ID NO:2 increases cell proliferation in a concentration-dependent manner (FIG. 1, "oligo 1"). When the splenocytes were incubated with the phosphorothioate oligonucleotide of SEQ ID NO:2 in the presence of 0.5% cyclodextrins, the level of cell proliferation decreased significantly (FIG. 1, "oligo 1+HPCD", "oligo 1+HECD", "oligo 1+Encapsin"). At 1 μg/ml, the levels of cell proliferation were reduced to almost the basal levels and at 10 μg/ml, the levels were reduced by approximately 30%. All the three cyclodextrin analogs reduced cell proliferation to similar levels. There was no significant change in [$^3$H] thymidine incorporation at 0.1 μg/ml of the phosphorothioate oligonucleotide of SEQ ID NO:2 (FIG. 1). When cyclodextrin analogs alone were added to the splenocytes, no significant change in [$^3$H] thymidine incorporation was observed, indicating that cyclodextrin analogs by themselves have no effect on cell proliferation.

Figure 2:
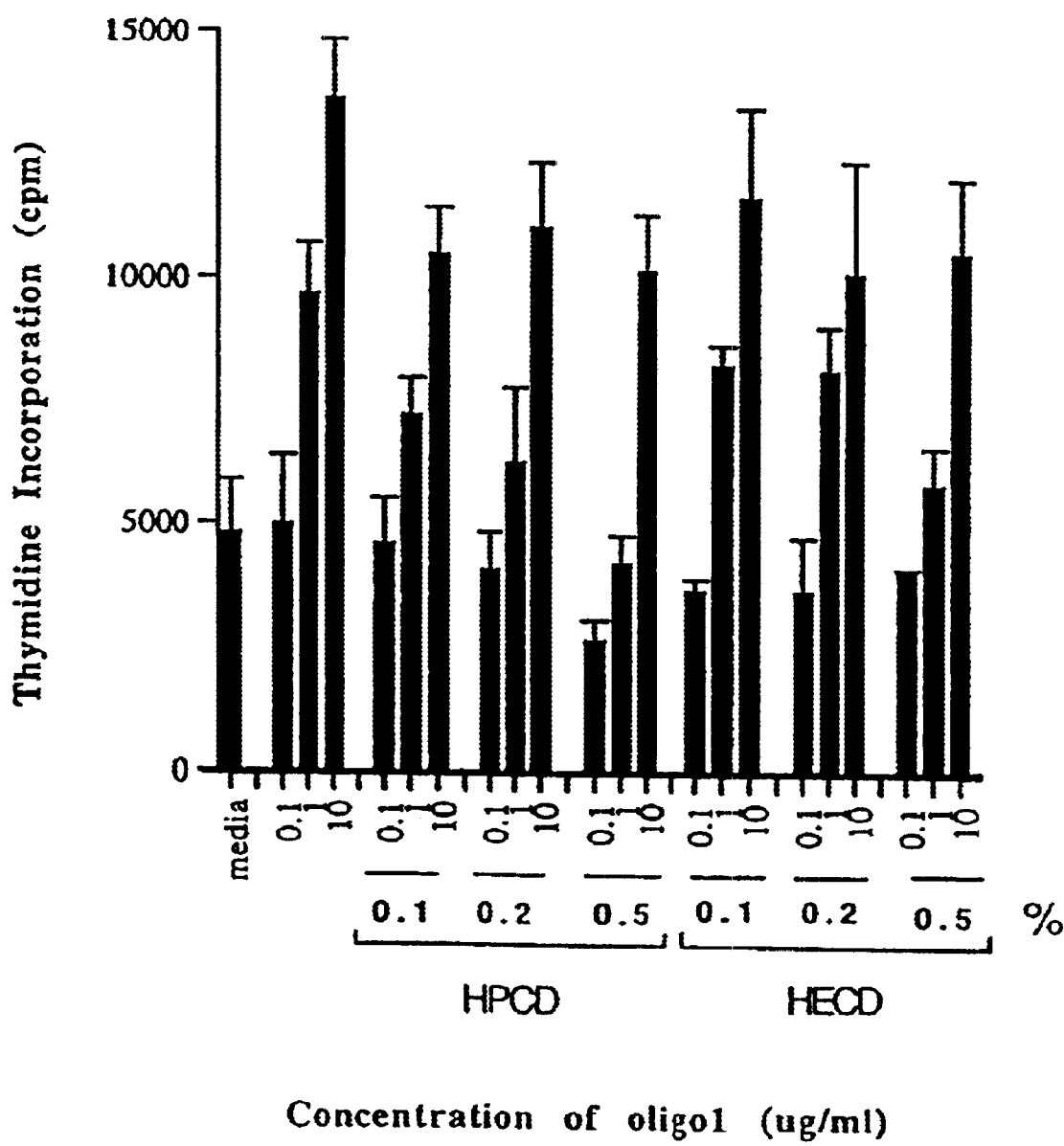
FIG. 2 shows the effect of different concentrations of cyclodextrins on modulation of cell proliferation induced by the phosphorothioate oligonucleotide of SEQ ID NO:2. Results are presented as means±standard deviation of triplicate experiment.

As shown in FIG. 2, the immunostimulatory response reducing effects of the cyclodextrins were concentration-dependent. Incubation of the cells with higher concentrations of cyclodextrins, such as 1%, results in cytotoxicity (Zhao et al. (1995) *Antisense Research & Dev.* 5 #3 In press). For that reason the cyclodextrin analogs were used at 0.5% concentration in further in vitro cell culture studies.

Figure 3:
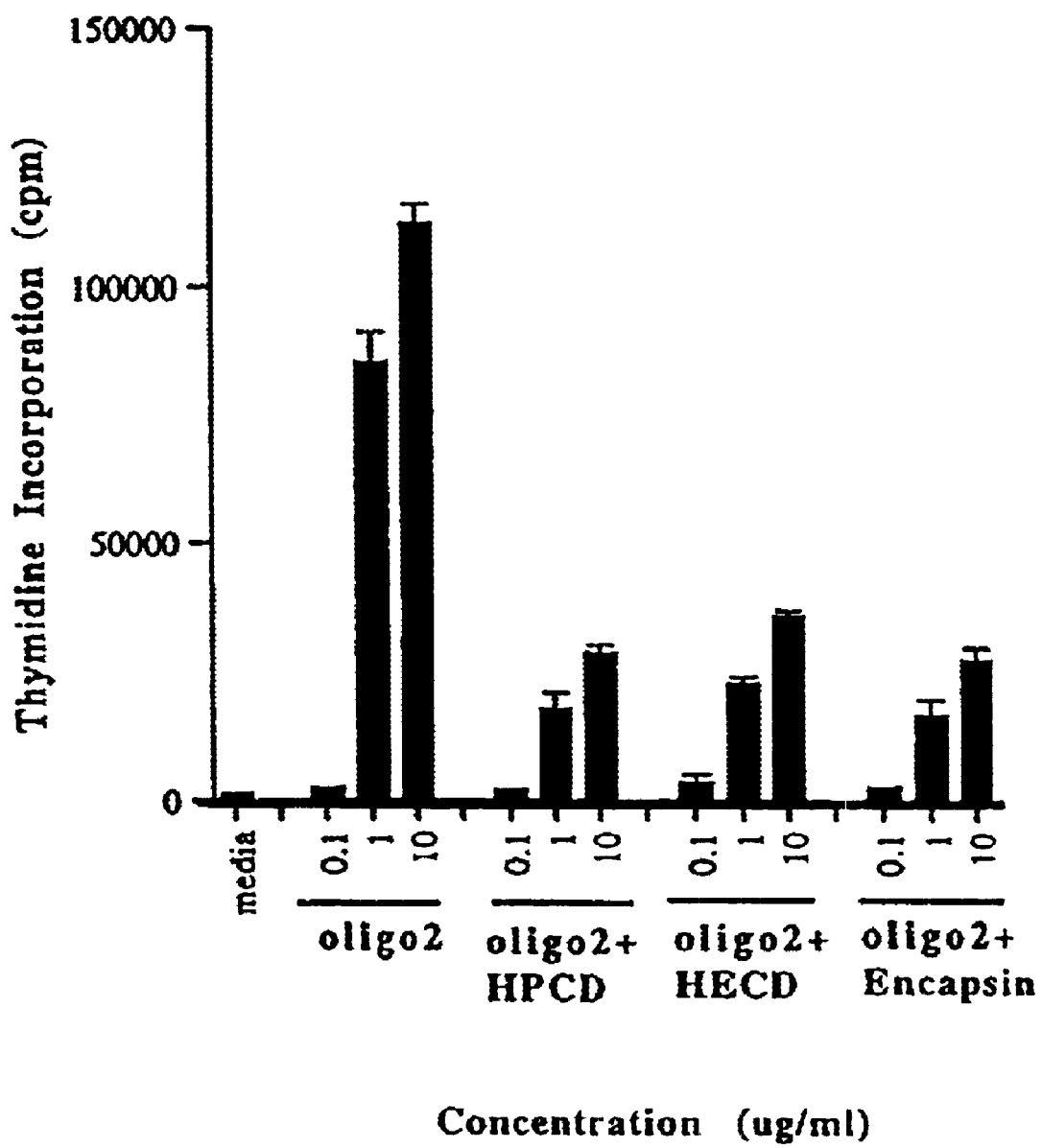
FIG. 3 shows the effect of cyclodextrins on cell proliferation induced by the phosphorothioate oligonucleotide of SEQ ID NO:4. Results are presented as means±standard deviation of triplicate experiment.

The phosphorothioate oligonucleotide of SEQ ID NO:4 is a 20-mer that contains multiple 5'-CG-3' motifs, which has been shown to induce an immunostimulatory response both in vitro and in vivo (Krieg et al. (1995) supra. FIG. 3 shows that when splenocytes were treated with 1 or 10 μg/ml of the phosphorothioate oligonucleotide of SEQ ID NO:4 alone, a dramatic increase in cell proliferation was observed. When cyclodextrin analogs (0.5%) were included in the cell culture, the increase in cell proliferation induced by the phosphorothioate oligonucleotide of SEQ ID NO:4 was markedly reduced. The effect of cyclodextrin and cyclodextrin analogs on other phosphorothioate oligonucleotides was similar, indicating that the immunostimulatory response-reducing effect of cyclodextrins is not restricted to a particular phosphorothioate oligonucleotide sequence.

B. Cell Cycle Analysis

1. In vitro Studies

Murine splenic lymphocytes were cultured for 48 hours in the presence of phosphorothioate oligonucleotides and/or cyclodextrin analogs at a density of $5 \times 10^5$ cells/tube, in 250 μl RPMI complete medium. After 48 hours of culture, cells were washed with FACS buffer [1×Hank's Balanced Salt Solution (HBSS) supplemented with 1% bovine serum albumin (BSA) and 0.1% sodium azide], fixed with 70% cold alcohol with immediate mixing, and then kept on ice for 30 minutes. After fixation, cells were washed twice and resuspended with 200 μl PBS and treated with 50 μl of RNAse (10 mg/ml, DNAase free) at 37° C. for 30 minutes. Propidium iodide (50 μg/ml) was added to the cells before flow cytometry analysis. Flow cytometric data on 10,000 viable cells were acquired in histogram on an Epics XL flow cytometer (Coulter, Hialeah, Fla.) and analyzed by Epics XL, version 1.5, software and multicycle software (Phoenix Flow Systems, San Diego, Calif.) after gating on living cells by forward scatter versus side scatter and excluding doublets. The experiments were done in triplicate.

The phosphorothioate oligonucleotide of SEQ ID NO:2 was used at 10 μg/ml to induce cell proliferation. Consistent with the results of thymidine incorporation, Table 1 shows that there was a significant increase (44.8%) in the percentage of cells in the S/G2 phases of the cell cycle 48 hours after in vitro treatment with the phosphorothioate oligonucleotide of SEQ ID NO:2 compared with medium alone. When cyclodextrin analogs were also included in the cell culture (0.5%), the increase in cells in the S/G2 phases of the cell cycle was less dramatic compared with the phosphorothioate oligonucleotide of SEQ ID NO:2 alone. These results indicate that cyclodextrin analogs can reduce the stimulation of cell proliferation induced by phosphorothioate oligonucleotide of SEQ ID NO:2.

TABLE 1

|  | % cells in G0/G1 | % cells in G2/S | Increase |
| --- | --- | --- | --- |
| MEDIUM | 84.6 ± 0.3 | 15.4 ± 0.3 | control |
| SEQ ID NO:2 | 77.7 ± 1.0 | 22.3 ± 1.0 | 44.8% |
| SEQ ID NO:2 + HPCD | 82.9 ± 0.1 | 17.1 ± 0.1 | 11% |
| SEQ ID NO:2 + HECD | 82.0 ± 0.3 | 18.0 ± 0.3 | 16.8% |
| SEQ ID NO:2 + ENCAP | 82.0 ± 0.3 | 18.0 ± 0.3 | 16.8% |

2. In vivo Studies

Male CD1 mice (4–5 weeks, 20–22 g, Charles river, Wilmington, Mass.) were used in this study. The animals were fed with commercial diet and water ad libidum and were kept at the animal facility of the University of Massachusetts Medical Center (Worcester, Mass.). For in vivo studies, phosphorothioate oligonucleotides (final concentration 4 mg/ml) were mixed with 5% of the cyclodextrin HPCD or HECD in sterile PBS, sonicated at 4° C. for 1 hour, followed by incubation at 4° C. overnight. The phosphorothioate oligonucleotide, either in plain PBS or mixed with cyclodextrin, was injected into mice intraperitoneally, in a volume of 0.25 ml (1 mg/mouse). After 24 hr (in the case of the phosphorothioate oligonucleotide of SEQ ID NO:4) and 48 hr (in the case of the phosphorothioate oligonucleotide of SEQ ID NO:2), mice were sacrificed and spleens were collected and prepared for further studies. Two or three mice were studied for each condition and analyzed individually.

Spleens from in vivo treated mice were harvested and single cell suspensions were set in culture in RPMI complete medium ($10^6$ cells/tube in 1 ml RPMI). After 4 hours of culture, cells were washed with FACS buffer and fixed for cell cycle analysis as described above. The experiments were done in duplicate.

As shown in Table 2, cell cycle analysis showed that there was approximately 30% increase in the percentage of cells in G2/S phases in phosphorothioate oligonucleotide of SEQ ID NO:2-treated mice compared with PBS-treated mice. Injection of HPCD along with the phosphorothioate oligonucleotide of SEQ ID NO:2 reduced the number of cells cycling, in a concentration-dependent manner. When 5 and 10% HPCD was added in the absence of phosphorothioate oligonucleotide, the levels of the cells in G2/S were similar to those of vehicle alone (PBS).

TABLE 2

|  | % cells in G0/G1 | % cells in G2/S | Increase |
| --- | --- | --- | --- |
| PBS | 86.4 ± 0.1 | 13.6 ± 0.1 | control |
| SEQ ID NO:2 | 82.0 ± 1.2 | 18.0 ± 1.2 | 32% |
| SEQ ID NO:2 + 2.5% HPCD | 84.5 ± 1.7 | 15.5 ± 1.7 | 14% |
| SEQ ID NO:2 + 5% HPCD | 85.7 ± 0.7 | 14.3 ± 0.7 | 5% |
| SEQ ID NO:2 + 10% HPCD | 86.7 ± 2.3 | 13.3 ± 2.3 | 0% |

Similar experiments were performed with the phosphorothioate oligonucleotide of SEQ ID NO:4. When the phosphorothioate oligonucleotide of SEQ ID NO:4 was injected at the same dose as the phosphorothioate oligonucleotide of SEQ ID NO:2 (50 mg/Kg), noticeable bloody exudate and congestion in abdominal cavities was observed, indicating toxicity. In order to reduce the toxicity, 25 mg/Kg of the phosphorothioate oligonucleotide of SEQ ID NO:4 was injected into the animals. Cell cycle analysis shows that the phosphorothioate oligonucleotide of SEQ ID NO:4 alone stimulated cell proliferation but, when it was mixed with 5% HPCD, the stimulation was reduced to the same levels as the vehicle alone (PBS) (Table 3).

TABLE 3

|  | % cells in G0/G1 | % cells in G2/S | Increase |
| --- | --- | --- | --- |
| PBS | 77.7 ± 0.7 | 22.3 ± 0.7 | control |
| SEQ ID NO:4 | 68.5 ± 0.5 | 22.7 ± 0.5 | 41% |
| SEQ ID NO:4 + 5% HPCD | 77.3 ± 0.5 | 22.7 ± 0.5 | 1% |

EXAMPLE 3

Spleen Size

Figure 4:
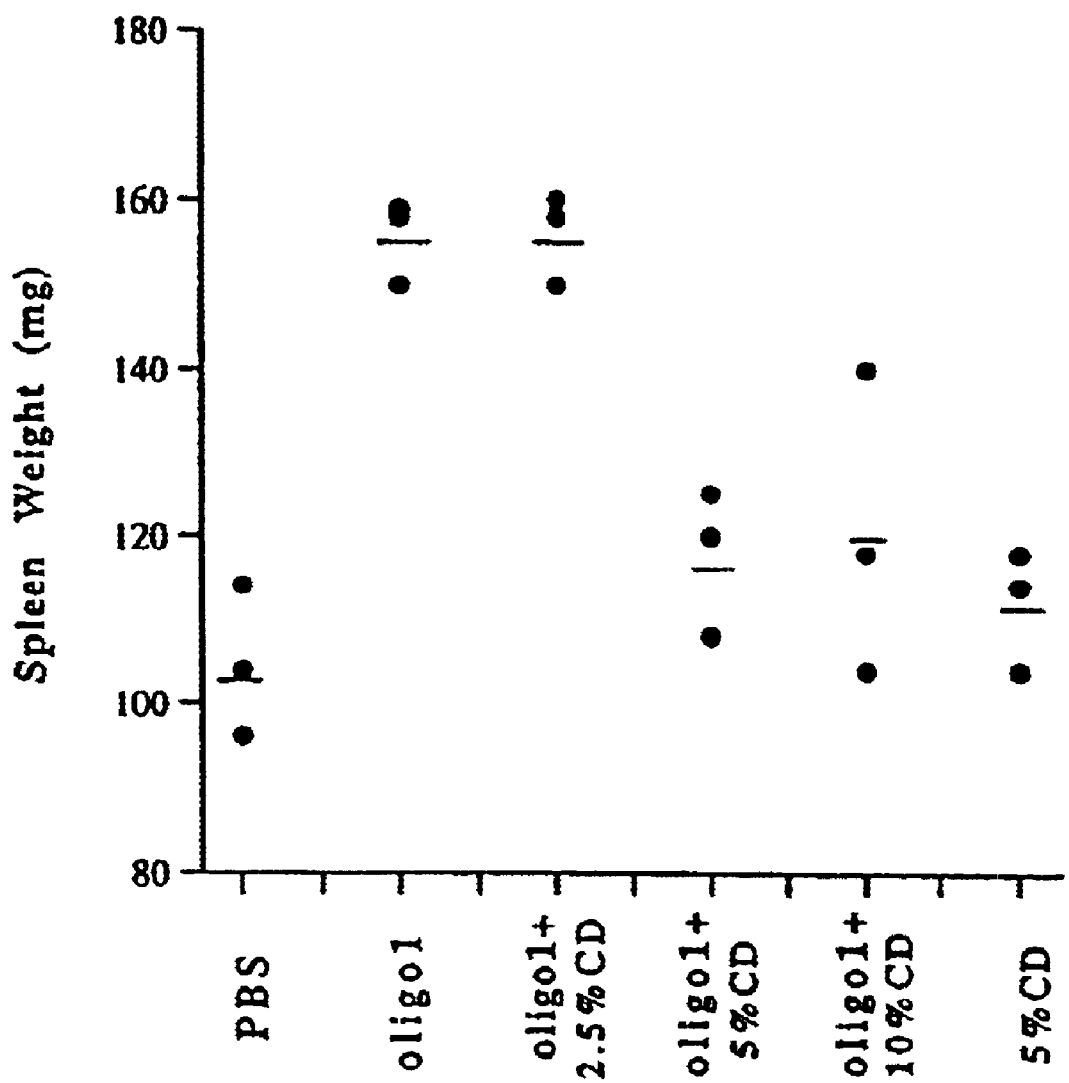
FIG. 4 shows the spleen weights of three animals after injection of the phosphorothioate oligonucleotide of SEQ ID NO:2, in the absence or in the presence of cyclodextrins. PBS represents the vehicle alone and 5% CD represents the HPCD with no oligomer. The bar represents the mean weight of each group.
Figure 6:
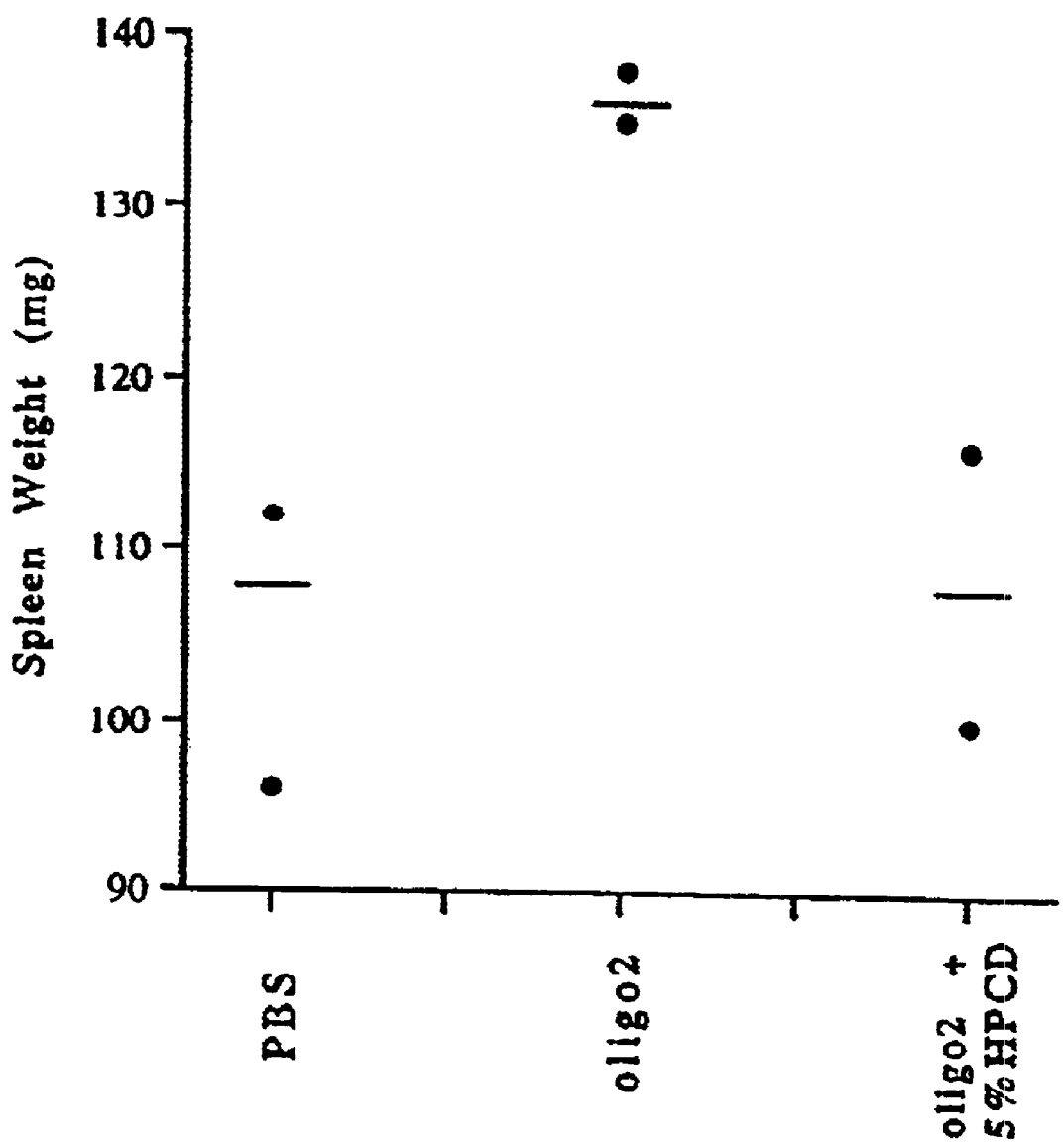
FIG. 6 shows spleen weights of two animals after injection of the phosphorothioate oligonucleotide of SEQ ID NO:4, alone or in the presence of 5% HPCD. The bar represents the mean weight of each group.

The weights of the spleens from phosphorothioate oligonucleotide of SEQ ID NO:2-treated mice were about 1.5 times in size as the PBS-treated mice ((FIG. 4). There was no significant reduction in spleen weight when 2.5% HPCD was used together with the phosphorothioate oligonucleotide of SEQ ID NO:2. However, when HPCD was used at concentrations of 5% or 10% together with the phosphorothioate oligonucleotide of SEQ ID NO:2, there was a significant decrease in spleen weight compared to the phosphorothioate oligonucleotide of SEQ ID NO:2 alone (FIG. 4). FIG. 6 shows that the phosphorothioate oligonucleotide of SEQ ID NO:4 alone induced splenomegaly, which was reduced when the oligonucleotide was injected along with 5% HPCD. Injection of 5% HPCD alone had no effect on spleen weight compared to PBS-treated mice.

EXAMPLE 4

Immunoglobulin Synthesis

Spleens from in vivo treated mice were harvested and single cell suspensions were set in culture at a density of $10^6$ cells/ml, in 1 ml RPMI complete medium. After 24 hours of incubation, cell culture supernatants were harvested by centrifugation and the supernatants were assayed for IgG or IgM levels using a standard enzyme-linked-immunoabsorbent assay (ELISA). ELISA plates (96 wells) were coated with goat anti-mouse IgG or IgM (5 $\mu$/ml) diluted in PBS supplemented with 0.05% sodium azide (pH 9.6) overnight at 4° C., washed three times with PBS-T buffer (PBS supplemented with 0.05% Tween 20 and 0.25% BSA), and incubated with cell culture supernatants at 37° C. for 2 hours. A standard of mouse IgG and IgM (1 mg/ml) was diluted with PBS-T to provide a standard curve between 0 and 800 ng/ml. The plates were then washed three times with PBS-T buffer and incubated at 37° C. for 2 hours with goat anti-mouse IgG conjugated to alkaline phosphatase diluted 1:1000 with PBS-T buffer. After three washes with PBS-T buffer, phosphatase substrate (p-nitrophenylphosphate) in diethanolamine buffer (75 $\mu$l) was added to the plates which were then kept at room temperature for 1 hour. The colorimetric reaction was stopped by addition of 25 $\mu$l of 0.5 M sodium hydroxide. The optical density (405 nm) was measured using an automatic ELISA plate reader (Bio-Tek Instruments, Inc). IgG and IgM levels were calculated based on the standard curve. The experiments were done in quadruplicate.

Figure 5:
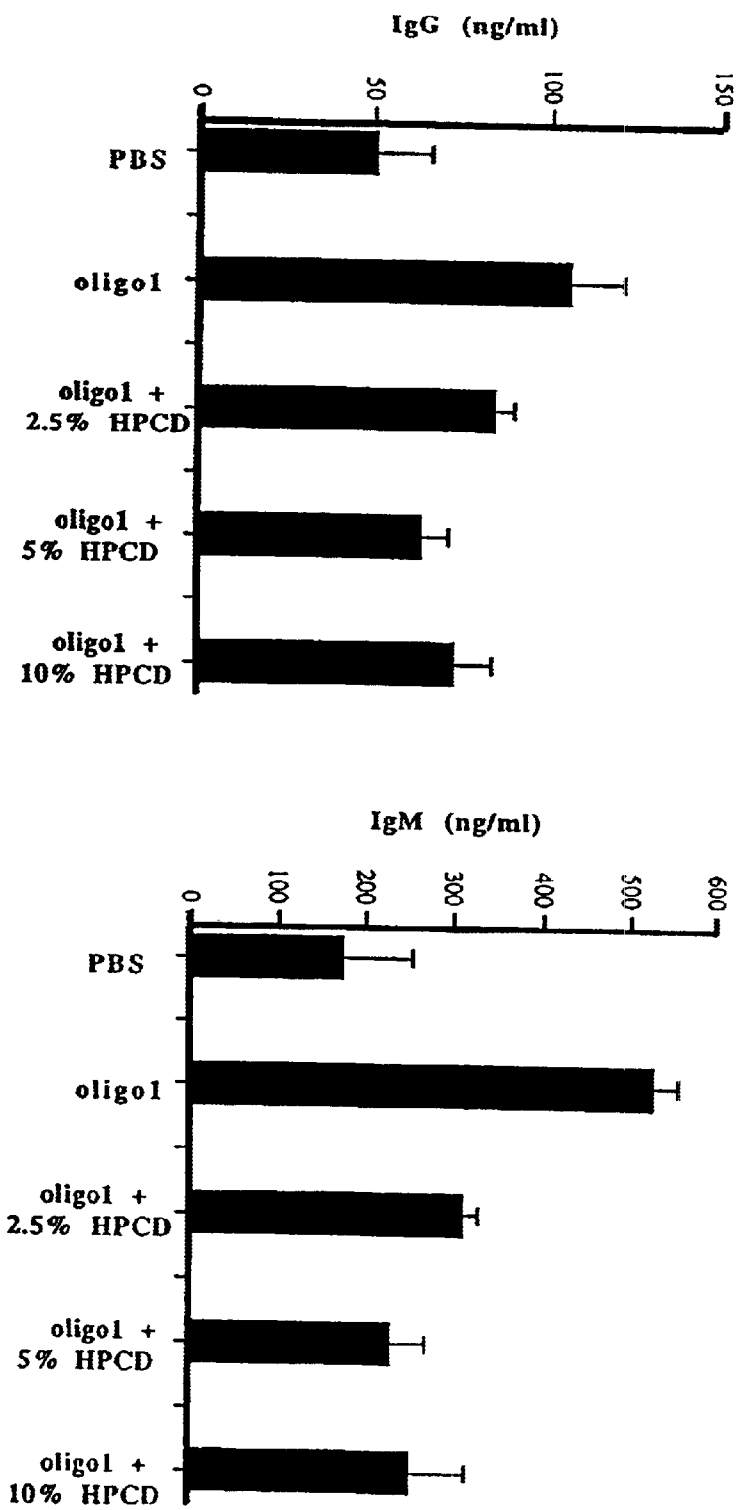
FIG. 5 shows IgG and IgM production measured 48 hours after injection into mice of the phosphorothioate oligonucleotide of SEQ ID NO:2, alone or in the presence of different concentrations of the cyclodextrin HPCD. Bars represents the standard deviation of triplicate experiments.
Figure 7:
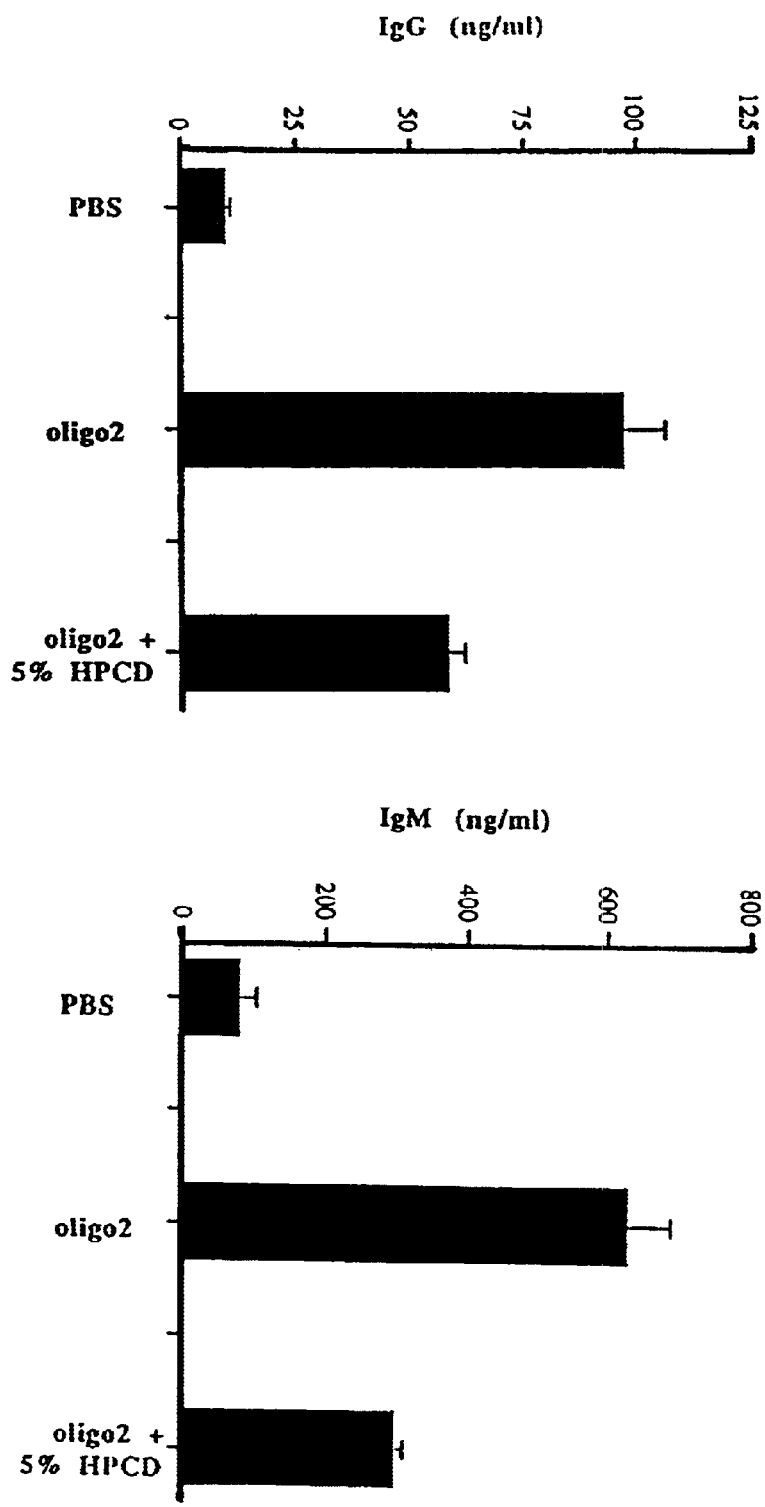
FIG. 7 shows IgG and IgM production measured 48 hours after injection of the phosphorothioate oligonucleotide of SEQ ID NO:4, alone or in the presence of 5% HPCD. Bars represents the standard deviation of triplicate experiments.

When the spleen lymphocytes were measured for immunoglobulin production, there was a highly significant increase in production of both IgG and IgM from mice injected with the phosphorothioate oligonucleotide of SEQ ID NO:2 compared to vehicle alone (FIG. 5). When the oligonucleotide was injected along with HPCD, there was a concentration-dependent reduction in IgG and IgM production. Measurement of IgG and IgM antibodies shows that the phosphorothioate oligonucleotide of SEQ ID NO:4 increases production of these antibodies by approximately 10 fold (FIG. 7). FIG. 7 also shows that in the presence of 5% HPCD, antibody production was significantly decreased.

EXAMPLE 5

1. Preparation of Protein-cyclodextrin Complexes

Proteins are mixed with cyclodextrin analogs in sterile phosphate buffered saline (PBS). The formation of the complex is measured by light scattering as described by Brewster et al. (*Pharmaceutical Research* (1991) 8:792–795). Briefly, a solution of the protein (5 mg/ml) is incubated with increasing concentrations of cyclodextrin (0–40%). Light scattering measurements indicate the concentration of cyclodextrin required to form a complex with the protein.

2. In vitro Experiments

Mouse spleen is taken from male CD1 mouse (4–5 weeks). Single cell suspensions are prepared by gently mincing with frosted ends of glass slides and then resuspending in RPMI complete medium [RPMI 1640 medium supplemented with 10%-heat inactivated (56° C. for 30 minutes) fetal bovine serum, 2 mM glutamine, 100 $\mu$g/ml streptomycin, 100 U/ml penicillin, and 50 $\mu$M 2-mercaptoethanol]. After plating the cells in 96-well dishes at a density of $10^6$ cells/ml, proteins (or other compounds) are added to the cells at different concentrations. First, the effect of these proteins on cell proliferation and antibody production is measured as described in Examples 2 through 4 above. Once the immune stimulation of a protein (or other compounds) is established, cyclodextrin and analogs are complexed to the protein order to induce suppression of immune stimulation.

3. In vivo Experiments

Male CD1 mice (4–5 weeks, 20–22 g, Charles River, Wilmington, Mass.) are used. Protein (or other compound) either in plain phosphate buffered saline or complexed with 5% of cyclodextrin are injected into mice intraperitoneally, in a volume of 0.25 ml (1 mg/mouse). After 24 hr to 48 hr, mice are sacrificed and spleens are collected and prepared for further studies. Three mice are studied for each condition. Cell proliferation, cell cycle analysis, and antibody production are measured as described in Examples 2 through 4 above.

Although this invention has been described in detail above in terms of a number of exemplary embodiments, those skilled in the art will readily appreciate that the exemplary embodiments may be modified in many ways without materially departing from the novel teachings and advantages of the invention. Accordingly, all such modifications are intended to be included within the scope of this invention as defined in the following claims.

What is claimed is:

1. A method of reducing an immunostimulatory response of a mammal to a phosphorothioate oligonucleotide which comprises the steps of:

a) administering a therapeutic formulation containing the phosphorothioate oligonucleotide and a cyclodextrin concentration of greater than 2.5% to the mammal; and b) monitoring the immune response of the mammal, wherein the immunostimulatory response of the mammal to the phosphorothioate oligonucleotide is reduced.

2. The method of claim 1 wherein the cyclodextrin is selected from the group consisting of a β-cyclodextrin, a γ-cyclodextrin, a substituted cyclodextrin, and a derivative of a cyclodextrin.

3. The method of claim 2 wherein the β-cyclodextrin is selected from the group consisting of 2-hydroxypropyl-β-cyclodextrin and 2-hydroxyethyl-β-cyclodextrin.

4. The method of claim 2 wherein the γ-cyclodextrin is hydroxypropyl-γ-cyclodextrin.

5. The method of claim 2 wherein the derivative of the cyclodextrin is selected from the group consisting of a β-cyclodextrin polysulfate and a γ-cyclodextrin polysulfate.

6. The method of claim 1 wherein the therapeutic formulation contains a mixture of cyclodextrins.

7. The method of claim 1 wherein the phosphorothioate oligonucleotide is modified.

8. A method of reducing an immunostimulatory response of a mammal to protein comprising the steps of:

a) administering a therapeutic formulation containing the protein a cyclodextrin to the mammal, the cyclodextrin having a concentration of greater than 5%; and b) monitoring the immune response of the mammal after administration of the formulation, wherein the immunostimulatory response of the mammal to the protein in the formulation is reduced.

9. The method of claim 8, wherein the therapeutic formulation comprises a protein-cyclodextrin complex.

* * * * *

UNITED STATES PATENT AND TRADEMARK OFFICE
CERTIFICATE OF CORRECTION

PATENT NO.   : 6,667,293 B1                                               Page 1 of 1
DATED        : December 23, 2003
INVENTOR(S)  : Quiyan Zhao et al.

It is certified that error appears in the above-identified patent and that said Letters Patent is hereby corrected as shown below:

<u>Column 18,</u>
Line 38, after "protein", insert -- and --.

Signed and Sealed this

Twentieth Day of April, 2004

JON W. DUDAS
*Acting Director of the United States Patent and Trademark Office*